United States Patent [19]

Dorn

[11] 4,380,544
[45] Apr. 19, 1983

[54] 1,3-DIOXOLANE COMPOUNDS AND THEIR USE AS FUNGICIDES

[75] Inventor: Franz Dorn, Dielsdorf, Switzerland

[73] Assignee: Hoffmann-La Roche Inc., Nutley, N.J.

[21] Appl. No.: 361,682

[22] Filed: Mar. 25, 1982

[30] Foreign Application Priority Data

Mar. 30, 1981 [CH] Switzerland .......................... 2142/81
Feb. 11, 1982 [CH] Switzerland ............................ 855/82

[51] Int. Cl.³ .................... A01N 43/40; C07D 405/06
[52] U.S. Cl. ...................................... 424/263; 546/283
[58] Field of Search ......................... 546/283; 424/263

[56] References Cited

U.S. PATENT DOCUMENTS

| | | | |
|---|---|---|---|
| 3,661,917 | 5/1972 | Kaiser et al. | 260/293.73 |
| 3,743,737 | 7/1973 | Kaiser et al. | 424/267 |
| 4,079,062 | 3/1978 | Van Reet et al. | 71/92 |
| 4,160,838 | 7/1979 | Van Reet et al. | 424/269 |
| 4,262,000 | 4/1981 | Holmwood et al. | 424/263 |

FOREIGN PATENT DOCUMENTS 2015524 9/1979 United Kingdom .

Primary Examiner—John M. Ford
Assistant Examiner—Bernard Dentz
Attorney, Agent, or Firm—Jon S. Saxe; George M. Gould; John J. Maitner

[57] ABSTRACT

1,3-Dioxolane derivatives of the formula

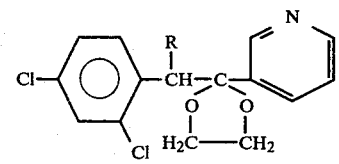

I wherein R is hydrogen or $C_{1-4}$-alkyl, and acid addition salts of these compounds, a process for their preparation, fungicidal compositions containing these compounds as the active ingredient and methods for the use of such compounds or compositions for combatting fungi in agriculture and in horticulture are disclosed.

9 Claims, No Drawings

1,3-DIOXOLANE COMPOUNDS AND THEIR USE AS FUNGICIDES

SUMMARY OF THE INVENTION

This invention relates to 1,3-dioxolane compounds of the formula

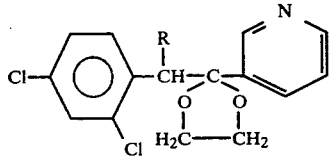

wherein R is hydrogen or $C_{1-4}$-alkyl, and acid addition salts thereof.

This invention also relates to fungicidal compositions containing the compounds of formula I as the active ingredient and to methods for the use of such compounds and compositions in combatting plant fungi.

DETAILED DESCRIPTION OF THE INVENTION

The invention is concerned with compounds of the formula

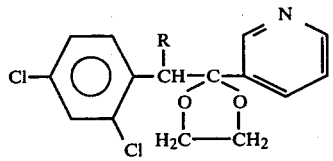

wherein R is hydrogen or $C_{1-4}$-alkyl, and acid addition salts thereof.

The compounds of formula I and their acid addition salts possess fungicidal properties and are suitable as fungicidal agents, especially for use in agriculture and in horticulture.

As used herein the term "$C_{1-4}$-alkyl" denotes not only straight-chain but also branched-chain alkyl groups containing from 1 to 4 carbon atoms, such as, methyl, ethyl, n-propyl, isopropyl, n-butyl, isobutyl, sec-butyl and tert-butyl. Of the $C_3$- and $C_4$-alkyl groups there are generally preferred the straight-chain groups.

When R is $C_{1-4}$-alkyl, this group is preferably $C_{1-3}$-alkyl, especially methyl.

An especially preferred compound of formula I is 3-[2-(2,4-dichlorobenzyl)-1,3-dioxolan-2-yl]pyridine.

Since the compounds of formula I contain an asymmetric carbon atom when R is $C_{1-4}$-alkyl, they can exist as optical antipodes. Formula I is, therefore, intended to include the optical isomers as well as racemic mixtures.

Exemplary of the acid addition salts of the compounds of formula I are physiologically acceptable salts. These include, in particular, salts formed with inorganic or organic acids such as hydrochloric acid, nitric acid, phosphoric acid, mono- and bifunctional carboxylic acids and hydroxycarboxylic acids, for example, acetic acid, maleic acid, succinic acid, fumaric acid, tartaric acid, citric acid, salicyclic acid, sorbic acid and lactic acid, and sulfonic acids, for example 1,5-naphthalene-disulfonic acid. Salts of this type are prepared in a known manner.

The compounds of formula I and acid addition salts thereof can be prepared by reacting a ketone of the formula

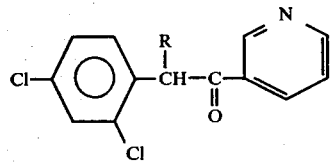

wherein R is as previously described, with ethylene glycol and, if desired, converting a compound of formula I into an acid addition salt thereof.

The reaction is conveniently carried out in an organic solvent, in the presence of an acid catalyst and in a temperature range between 80° C. and 140° C. Suitable solvents include aromatic hydrocarbons, for example, benzene, toluene, xylenes and the like. Such solvents permit the continuous removal by distillation of the water formed from the reaction mixture. Acid catalysts which can be employed in the process for preparing the compounds of formula I include mineral acids such as sulfuric acid and hydrochloric acid or sulfonic acids such as p-toluenesulfonic acid. Since the starting material of formula II is basic, the acid catalyst is advantageously used in slight excess.

For the preparation of the acid addition salts, the compounds of formula I can be reacted with inorganic or organic acids such as hydrochloric acid, nitric acid, phosphoric acid, mono- or bifunctional carboxylic or hydroxycarboxylic acids or sulfonic acids. The salt formation can be carried out without previous isolation of the compound of formula I from the reaction mixture, or it can be carried out separately. In the latter case, ethylene glycol or a non-protic solvent, such as an ether, for example, diethyl ether, tetrahydrofuran, or the like, is conveniently used as the diluent or solvent.

The isolation and purification of the compounds of formula I or acid addition salts thereof can be carried out by conventional methods which are well known to one of ordinary skill in the art.

The ketones of formula II which are used as starting materials can be prepared according to methods known per se; for example, by reacting an alkyl ester of nicotinic acid with an ester of 2,4-dichlorophenylacetic acid as described in DOS No. 2 221 546, pp. 6, 19, 21–22, 25 and 40. Preferably the ketones of formula II can be prepared by one of the procedures described below.

(a) Reacting a halide of the formula

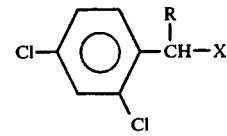

wherein R is as described previously and X is chlorine, bromine or iodine, with a compound of the formula

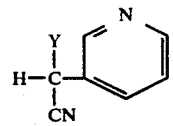

wherein Y is a disubstituted amino group, e.g. dimethylamino, diethylamino, piperidino or morpholino, and hydrolyzing the product, of the formula wherein $R^1$ is $C_{1-4}$-alkyl and Z is a leaving group, preferably chlorine, bromine or iodine, to give a ketone of formula II wherein R is $C_{1-4}$-alkyl.

The following Reaction Scheme illustrates the two process variants (a) and (b) for the preparation of the ketones of formula II:

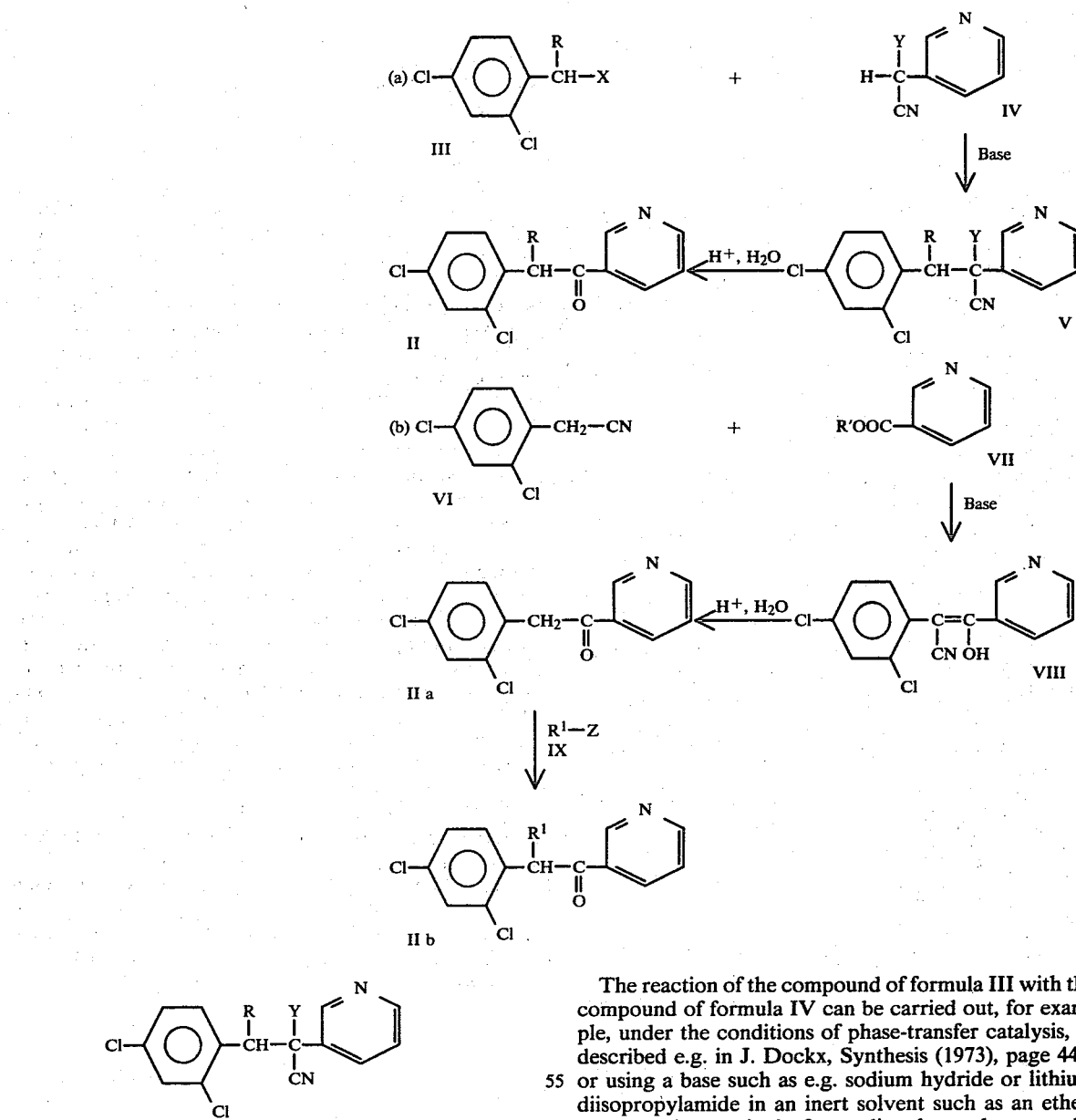

wherein R and Y are as described previously.

(b) Reacting 2,4-dichlorobenzyl cyanide (VI) with a lower alkyl ester of nicotinic acid (VII) to give α-(2,4-dichlorophenyl)-β-hydroxy-β-(3-pyridyl)-acrylonitrile (VIII) and treating this intermediate with a strong acid to give the ketone of formula II wherein R is hydrogen and, if desired, treating the last-mentioned compound with an alkylating agent of the formula $R^1$—Z         IX The reaction of the compound of formula III with the compound of formula IV can be carried out, for example, under the conditions of phase-transfer catalysis, as described e.g. in J. Dockx, Synthesis (1973), page 441, or using a base such as e.g. sodium hydride or lithium diisopropylamide in an inert solvent such as an ether, for example, tetrahydrofuran, dimethoxyethane, or the like. The reaction is run at a temperature between about −70° C. and about 50° C., preferably between −30° C. and room temperature, and with the exclusion of water. The intermediate of formula V can be converted into the ketone of formula II by hydrolysis, for example by conventional treatment with an aqueous acid. As acids there come into consideration for this purpose especially strong inorganic acids such as sulfuric acid, hydrochloric acid and hydrobromic acid as well as sulfonic acids such as benzenesulfonic acid and p-toluenesulfonic acid. The hydrolysis is conveniently carried out at temperatures in the range from about 20° C. to the reflux temperature of the reaction mixture, preferably between 80° C. and 100° C.

In the compound of formula VII used in process variant (b) R' preferably is $C_{1-4}$-alkyl, especially ethyl. The reaction of the compound of formula VI with the compound of formula VII is carried out in the presence of a base, preferably sodium ethylate, conveniently in an organic diluent such as ethanol, benzene or toluene. The intermediate of formula VIII is converted into the ketone of formula IIa by treatment with a strong acid such as sulfuric acid, hydrochloric acid or a sulfonic acid, for example, methanesulfonic acid or p-toluenesulphonic acid, in the presence of water.

In the alkylation of the ketone of formula IIa to give a ketone of formula IIb, the first-mentioned ketone is advantageously converted into an anion with a base such as sodium hydride or lithium diisopropylamide in a diluent, preferably an aprotic organic solvent such as tetrahydrofuran, dimethoxyethane or dimethylformamide. The anion formation is carried out at temperatures in the range of from about −70° C. to about 50° C. The anion is then treated with the alkylating agent of formula IX.

The isolation and optional purification of the intermediates or starting materials can be carried out according to conventional methods.

The compounds of formula I and their acid addition salts possess fungicidal activity and can accordingly be used for combatting fungi in agriculture and in horticulture. They are especially suitable for eliminating or combatting phytopathogenic fungi on parts of plants, for example, leaves, stems, roots, tubers, fruits or flowers, and on seeds as well as in the soil. The compounds of formula I are especially active in the control of *Botrytis cinerea* (grey rot), of powdery mildew fungi such as, for example, *Uncinula necator* (powdery mildew of vines), *Erysiphe cichoracearum* (powdery mildew of cucumbers), *Podosphaera leucotricha* (powdery mildew of apples) and *Erysiphe graminis* (powdery mildew of barley), of *Venturia inaequalis* (apple scab), of *Helminthosporium oryzae* (brown spot disease of rice) and of harmful fungi of the genera Puccinia, Uromyces, Rhizoctonia, Penicillium, Septoria and Cercospora.

Furthermore, certain compounds of formula I possess a pronounced activity against wood-destroying fungi such as, for example, *Coniophora puteana* and *Gloeophyllum trabeum*.

The compounds of formula I of this invention possess local and/or systemic activity.

The compounds of formula I are active under greenhouse conditions at a concentration of 10 mg to 500 mg of active ingredient, that is, a compound of formula I, per liter of spray liquor. In the open air, they are advantageously applied in concentrations of 100 g to 2000 g of active ingredient per hectare and treatment.

This invention is also directed to plant fungicidal compositions comprising compatible inert carrier material and, as the active ingredient, one or more of the compounds of formula I. These compositions can be, for example, spray liquors, aqueous suspensions, emulsions, emulsifiable concentrates and powders. Depending on its type, a plant fungicidal composition of this invention contains from about 0.0001 percent to about 95 percent by weight, based on the weight of the total composition, of a compound or compounds of formula I as the active ingredient.

Examples of compatible inert carrier material include inert pulverous carrier materials such as, for example, kaolin, bentonite, talc, whiting, magnesium carbonate and siliceous earth; wetting or emulsifying agents and inert solvents.

For the preparation of pulverous fungicidal compositions, the inert pulverous carrier material can be admixed with the active ingredients (e.g. by grinding them together). In an alternate procedure, the inert pulverous carrier materials can be impregnated with a solution of the active ingredient with the solvent subsequently removed by evaporation, heating or aspiration under reduced pressure.

These powder compositions can be applied to plants to be protected in the form of dusts using standard apparatus. By the addition of wetting and/or dispersing agents to the pulverous fungicidal compositions, the compositions are readily wettable with water and, thus, can be used as aqueous suspension suitable for spray applications.

To prepare emulsifiable concentrates, the active ingredients can be mixed with an emulsifying agent or dissolved in an inert solvent and mixed with an emulsifier. Ready-for-use emulsions are prepared by dilution of such concentrates with water. These concentrates can contain from about 5 percent to about 95 percent by weight, and, preferably, from about 25 percent to about 75 percent by weight, based on the total weight of the concentrate, of active ingredient.

The fungicidal compositions of this invention can contain, in addition to the compounds of formula I, other active ingredients, for example, other fungicidal agents, insecticidal and acaricidal agents, bactericides, plant growth regulators, fertilizers and the like. Such combination compositions are useful either for broadening the spectrum of activity or for specifically influencing the plant growth. The compositions can be, for example, pulverous compositions or spray liquids depending on the field of application.

The fungicidal compositions of the present invention can be applied according to conventional application methods which are usual in plant protection or in agriculture. The method in accordance with the invention for the control of fungi comprises treating the locus to be protected, for example, plants, parts of plants or seeds, with an effective amount of a compound of formula I or a fungicidal composition in accordance with the invention.

The following Examples illustrate the present invention. All temperatures are given in degrees Centigrade.

I. PREPARATION OF THE ACTIVE INGREDIENTS

Example 1

2.25 g of 2,4-dichlorobenzyl 3-pyridyl ketone, 2.2 g of p-toluenesulfonic acid monohydrate and 1.0 g of ethylene glycol are heated at reflux for 24 hours in 20 ml of xylene, the resulting water being separated in a water separator. The mixture is then cooled, poured into 2N sodium hydroxide and extracted with diethyl ether, the organic phase is dried over anhydrous sodium sulfate and the solvent is removed under reduced pressure. The crude product is purified by chromatography on silica gel with n-hexane/ethyl acetate (1:1) to yield 3-[2-(2,4-dichlorobenzyl)-1,3-dioxolan-2-yl]pyridine, which melts at 76°–78°.

EXAMPLE 2

2 g of 2-(2,4-dichlorophenyl)-1-(3-pyridyl)-1-propanone are dissolved in 80 ml of toluene. After the addition of 1.05 g of concentrated sulfuric acid and 1.02 g of ethylene glycol, the mixture is heated at reflux. The water which is formed in the course of the reaction is separated using a water separator. After a reaction period of 4, 7 and 12 hours, an additional 1.5 g of ethylene glycol are added each time. After 15 hours, the mixture is cooled, the toluene phase is discarded, the lower viscous phase is diluted with 50 ml of methylene chloride and subsequently poured into 37.5 ml of 1N sodium hydroxide. Then it is back-extracted with methylene chloride and the organic phase is washed and dried over anhydrous sodium sulfate. After removal of the solvent, 3-[2-(2,4-dichloro-α-methyl-benzyl)-1,3-dioxolan-2-yl]pyridine is obtained as a brownish, highly viscous oil.

II. PREPARATION OF THE STARTING MATERIALS

Example 3

125 g of 2,4-dichlorobenzyl chloride are added at room temperature to a mixture of 700 g of 50% sodium hydroxide, 23 g of tetrabutylammonium iodide and 130 g of α-(3-pyridyl)-4-morpholineacetonitrile. After 2 hours the mixture is extracted with diethyl ether. After evaporation of the ether, the crude product, α-(2,4-dichlorobenzyl)-α-(3-pyridyl)-4-morpholineacetonitrile (m.p. 130°-132°), remains behind. The crude product is taken up in 300 ml of concentrated hydrochloric acid and the solution is heated to reflux temperature for 12 hours. The reaction mixture is made basic and extracted with ethyl acetate, and the organic phase is washed, dried over anhydrous sodium sulfate and concentrated. Crystallization from ethyl acetate/n-hexane yields 2,4-dichlorobenzyl 3-pyridyl ketone of melting point 78°-79°.

In an analogous manner, α-(3-pyridyl)-4-morpholineacetonitrile and 1-(2,4-dichlorophenyl)-1-bromoethane yields, via the isomer mixture of α-(2,4-dichloro-α-methylbenzyl)-α-(3-pyridyl)-4-morpholineacetonitrile, 2-(2,4-dichlorophenyl)-1-(3-pyridyl)-1-propanone as an oil.

Example 4

A solution of 303.7 g of 2,4-dichlorobenzyl cyanide in 373.6 g of ethyl nicotinate is added dropwise during 3½ hours to a boiling solution of 48.3 g of sodium in 1055 ml of ethanol. Then the mixture is heated at reflux for an additional 5 hours, stirred at room temperature for 16 hours, poured into ice/water and washed with diethyl ether. Subsequently 205 ml of acetic acid are added to the aqueous phase, whereby crystals of α-(2,4-dichlorophenyl)-β-hydroxy-β-(3-pyridyl)-acrylonitrile precipitate. These crystals are separated, washed with water and diethyl ether and then dried. The melting point of the purified α-(2,4-dichlorophenyl)-β-hydroxy-β-(3-pyridyl)-acrylonitrile is 187°-188°.

These crystals (286.8 g) are added portionwise to 1050 g of 75% sulfuric acid. The mixture is heated to 100°-120° for 3½ hours, then cooled, poured into water and adjusted to pH 9 by the addition of ammonia and the resulting crystals are filtered off under suction. After washing with water and n-hexane and drying at 40°/16 Torr, crystals of 2,4-dichlorobenzyl 3-pyridyl ketone of melting point 75°-76° are obtained.

Example 5

28 g of 2,4-dichlorobenzyl 3-pyridyl ketone are dissolved in 800 ml of dimethylformamide and treated portionwise at 0° with 5.5 g of sodium hydride (50% dispersion in oil). After 2 hours at room temperature, 14.9 g of methyl iodide are added and the mixture is stirred at room temperature for an additional 3 hours. Then the mixture is poured into water and extracted with diethyl ether, and the organic phase is washed and dried over anhydrous sodium sulfate and subsequently concentrated. The product is purified by chromatography on silica gel with n-hexane/ethyl acetate (1:2) to yield 2-(2,4-dichlorophenyl)-1-(3-pyridyl)-1-propanone as an oil.

In an analogous manner, 2,4-dichlorobenzyl 3-pyridyl ketone and ethyl bromide yield 2-(2,4-dichlorophenyl)-1-(3-pyridyl)-1-butanone as an oil.

III. FORMULATION EXAMPLES

Example 6

1. Sprayable powder appropriate for the compounds of formula I which are liquid or melt below 75°

|  | Parts by weight |
|---|---|
| Active ingredient of formula I | 50 |
| Hydrated silicic acid | 37 |
| Kaolin | 5 |
| Alkylphenol ethoxylate | 4 |
| Sodium polynaphthalenesulfonate | 4 |
|  | 100 |

The liquid or molten active ingredient is taken up on the hydrated silicic acid. The remaining additives are added and the mixture is finely ground in a suitable mill.

2. Sprayable powder appropriate for the compounds of formula I which melt above 75°

|  | Parts by weight |
|---|---|
| Active ingredient of formula I | 50 |
| Hydrated silicic acid | 5 |
| Kaolin | 42 |
| Sodium lauryl sulfate | 1 |
| Sodium lignosulfonate | 2 |
|  | 100 |

The ingredients are mixed with one another and the mixture is finely ground in a suitable mill.

3. Emulsifiable concentrate appropriate for the compounds of formula I which are liquid at 20°-25°

|  | Parts by weight |
|---|---|
| Active ingredient of formula I | 500 |
| Castor oil acetoxylate | 100 |
| Calcium dodecylbenzenesulfonate | 25 |
| Mixture of $C_{10}$—alkylbenzenes | ad 1000 parts by volume |

The components are mixed with one another until a clear solution is obtained.

I claim:
1. A compound of the formula

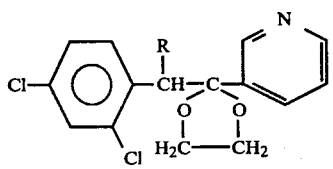

wherein R is hydrogen or $C_{1-4}$-alkyl, or an acid addition salt thereof.

2. 3-[2-(2,4-Dichlorobenzyl)-1,3-dioxolan-2-yl]pyridine.

3. 3-[2-(2,4-Dichloro-α-methyl-benzyl)-1,3-dioxolan-2-yl]pyridine.

4. A fungicidal composition comprising a compatible carrier material and, as the active ingredient, an amount which is effective as a fungicide of a compound of the formula

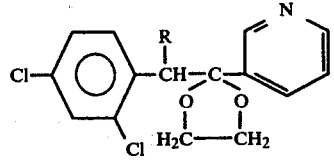

wherein R is hydrogen or $C_{1-4}$-alkyl,
or an acid addition salt thereof.

5. The fungicidal composition of claim 4 wherein the active ingredient is 3-[2-(2,4-dichlorobenzyl)-1,3-dioxolan-2-yl]pyridine.

6. The fungicidal composition of claim 4 wherein the active ingredient is 3-[2-(2,4-dichloro-α-methyl-benzyl)-1,3-dioxolan-2-yl]pyridine.

7. A method for combatting plant fungi which comprises treating the locus to be protected with the composition of claim 4.

8. The method of claim 7 wherein the active ingredient is 3-[2-(2,4-dichlorobenzyl)-1,3-dioxolan-2-yl]pyridine.

9. The method of claim 7 wherein the active ingredient is 3-[2-(2,4-dichloro-α-methyl-benzyl)-1,3-dioxolan-2-yl]pyridine.

* * * * *